(12) United States Patent
Needham

(10) Patent No.: US 6,200,598 B1
(45) Date of Patent: *Mar. 13, 2001

(54) TEMPERATURE-SENSITIVE LIPOSOMAL FORMULATION

(75) Inventor: David Needham, Durham, NC (US)

(73) Assignee: Duke University, Durham, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/099,668

(22) Filed: Jun. 18, 1998

(51) Int. Cl.$^7$ ............................ A61K 9/127; A61K 9/133
(52) U.S. Cl. ................ 424/450; 424/1.21; 424/9.321; 424/9.51; 424/94.3; 935/54
(58) Field of Search .................... 424/450, 1.21, 424/9.321, 9.51, 94.3; 935/54; 436/829

(56) References Cited

U.S. PATENT DOCUMENTS

| | | | |
|---|---|---|---|
| 4,828,837 | * | 5/1989 | Uster .................................. 424/450 |
| 4,906,476 | * | 3/1990 | Radhakrishnan ..................... 424/450 |
| 4,921,644 | * | 5/1990 | Lau ...................................... 264/41 |
| 4,921,706 | * | 5/1990 | Roberts ................................ 424/450 |
| 5,013,556 | * | 5/1991 | Woodle ................................ 426/450 |
| 5,077,056 | | 12/1991 | Bally et al. ......................... 424/450 |
| 5,080,904 | | 1/1992 | Iga et al. ............................. 424/450 |
| 5,094,854 | | 3/1992 | Ogawa et al. ....................... 424/423 |
| 5,277,913 | | 1/1994 | Thompson et al. ................. 424/450 |
| 5,683,715 | * | 11/1997 | Boni ..................................... 424/450 |
| 5,720,976 | | 2/1998 | Kim et al. ........................... 424/450 |
| 5,736,156 | * | 4/1998 | Burke ................................... 424/450 |
| 5,755,788 | | 5/1998 | Strauss ................................. 623/11 |
| 5,783,566 | * | 7/1998 | Mislick ................................. 514/44 |
| 5,810,888 | | 9/1998 | Fenn .................................... 607/154 |

FOREIGN PATENT DOCUMENTS

| | | | |
|---|---|---|---|
| WO 92/22249 | 12/1992 | (WO) | ............................. A61B/8/14 |
| WO 94/13265 | 6/1994 | (WO) | ............................. A61K/9/127 |
| WO 95/08986 | 4/1995 | (WO) | ............................. A61K/9/127 |

OTHER PUBLICATIONS

Kono; Temperature-sensitive liposomes: liposomes bearing poly (N-isopropylacrylamide) *Journal of Controlled Release* 30; 69–75 (1994).

Yatvin et al.; Design of Liposomes for Enhanced Local Release of Drugs by Hyperthermia *Science* 202:1290–1292 (Dec. 1978).

Weinstein et al.; Liposomes and Local Hyperthermia: Selective Delivery of Methotrexate to Heated Tumors *Science* 204:188–191 (Apr. 1979).

Liburdy et al.; Microwave-Stimulated Drug Release from Liposomes *Radiation Research* 103:266–275 (1985).

Tomita et al.; Temperature-sensitive release of adriamycin, an amphiphilic antitumor agent, from dipalmitoylphosphatidylcholine-cholesterol liposomes *Biochim Biophys. Acta* 978:185–190 (1989).

Oku et al.; Potential usage of thermosensitive liposomes for macromolecule delivery *Biochim. Biophys. Acta* 1191:389–391 (1994).

(List continued on next page.)

Primary Examiner—Gollamudi S. Kishore
(74) Attorney, Agent, or Firm—Myers Bigel Sibley & Sajovec, P.A.

(57) ABSTRACT

Temperature sensitive liposomes containing active agents are described. The liposomes comprise phospholipids and a surface active agent, such as a lysolipid, that increases the amount of active agent released by the liposome at the phase transition temperature of the liposome. Such liposomes are useful in methods of administering active agents using mild hyperthermic conditions.

24 Claims, 8 Drawing Sheets

OTHER PUBLICATIONS

Maruyama et al.; Enhanced delivery of doxorubicin to tumor by long–circulating thermosensitive liposomes and local hyperthermia *Biochim Biophys. Acta.* 1149:209–216 (1993).

Weinstein et al.; Phase Transition Release, A New Approach to the Interaction of Proteins with Lipid Vesicles *Biochim Biophys. Acta.* 647:270–284 (1981).

Demel et al.; The Function of Sterols in Membranes *Biochim. Biophys. Acta.* 457:109–132 (1976).

Yatvin et al.; Selective Delivery of Liposome–associated cis–Dichlorodiammineplatinum(II) by Heat and Its Influence on Tumor Drug Uptake and Growth *Cancer Research* 41:1602–1607 (May 1981).

Iga et al.; Heat–specific drug release of large unilamellar vesicle as hyperthermia–mediated targeting delivery *International J. Pharmaceutics* 57:241–251.

Bassett et al.; Use of Temperature–Sensitive Liposomes in the Selective Delivery of Methotreaxate and Cis–Platinum Analogues to Murine Bladder Tumor *Journal of Urology* 135:612–615 (1985).

Gaber et al.; Thermosensitive Sterically Stabilized Liposomes: Formulation and in Vitro Studies on Mechanism of Doxorubicin Release by Bovine Serum and Human Plasma *Pharmaceutical Research* 12:14071416.

Van Echteld et al.; Differential Miscibility Properties of Various Phosphatidylcholine/Lyshophosphatidylcholine Mixtures *Biochem Biophys Acta.* 595:71–80 (1980).

Klopfenstein et al.; Differential Scanning Calorimetry on Mixtures of Lecithin, Lysolecithin and Cholesterol; *Chemistry and Physics of Lipids* 13:215–222 (1974).

Devlin, B.P. et al., A Kinetic Study of the Polyelectrolyte–Induced Reorganization of Lipid Bilayers, *Am. Chem. Soc. Div. Polym. Chem.* vol. 28, No. 2, (1987), pp. 50–51.

Hristova, K., et al., Effect of Bilayer Composition On the Phase Behavior Liposomal Suspensions Containing Poly(ethylen glycol) Lipids, *Macromolecules,* vol. 28, No. 23 (1995) pp. 7693–7699.

International Search Report dated Nov. 24, 1999 for corresponding International application no. PCT/US99/12964.

Zhelev; "Material Property Characteristics for Lipid Bilayers Containing Lysolipid," *Biophysical Journal* 75:321–330 (Jul. 1998).

\* cited by examiner 1, 2-Dipalmitoyl-s n-Glycero-3-Phosphocholine (DPPC)

1-Palmitoyl-2-Hydoxy-sn-Glycero-3-Phosphocholine (MPPC)

1, 2-Distearoyl-sn-Glycero-3-Phosphoethanolamine-N-[Poly(ethylene glycol)2000] (DSPE-PEG2000)

TEMPERATURE-SENSITIVE LIPOSOMAL FORMULATION

This invention was made with Government support under National Institutes of Health grant NIH GM40162 and National Cancer Institute SPORE grant P50-CA68438. The Government may have certain rights to this invention.

FIELD OF THE INVENTION

The present invention relates to thermosensitive liposomes, and more specifically to liposomes comprising phospholipids and a surface active agent, wherein the liposomes release their contents at mild hyperthermic temperatures.

BACKGROUND OF THE INVENTION

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVs) are typically larger than 0.05 μm. Oligolamellar large vesicles and multilamellar large vesicles have multiple, usually concentric, membrane layers and are typically larger than 0.1 μm. Liposomes with several nonconcentric membranes, i.e., several small vesicles contained within a larger vesicle, are termed multivesicular vesicles.

Conventional liposomes are formulated to carry therapeutic agents, drugs or other active agents either contained within the aqueous interior space (water soluble active agents) or partitioned into the lipid bilayer (water-insoluble active agents). Copending U.S. patent application Ser. No. 08/795,100 discloses liposomes containing cholesterol in the lipid bilayer membrane, where an active agent is aggregated with a lipid surfactant to form micelles and the micelles are entrapped in the interior space of the liposome.

Active agents that have short half-lives in the bloodstream are particularly suited to delivery via liposomes. Many anti-neoplastic agents, for example, are known to have a short half-life in the bloodstream such that their parenteral use is not feasible. However, the use of liposomes for site-specific delivery of active agents via the bloodstream is limited by the rapid clearance of liposomes from the blood by cells of the reticuloendothelial system (RES).

Liposomes are normally not leaky but will become so if a hole occurs in the liposome membrane, if the membrane degrades or dissolves, or if the membrane temperature is increased to the phase transition temperature. The elevation of temperature (hyperthermia) at a target site in a subject to raise liposome temperature above the phase transition temperature, and thereby cause the release of the liposome contents, has been used for the selective delivery of therapeutic agents. Yatvin et al., Science 204:188 (1979). This technique is limited, however, where the phase transition temperature of the liposome is significantly higher than the normal tissue temperature.

It is accordingly desirable to devise liposome formulations capable of delivering therapeutic amounts of active agents in response to mild hyperthermic conditions.

SUMMARY OF THE INVENTION

In view of the foregoing, a first aspect of the present invention is a liposome containing an active agent. The liposome's lipid bilayer membrane contains phospholipids as the primary lipid source; lysolipids are contained in the bilayer membrane in an amount that increases the percentage of active agent released at the phase transition temperature, compared to that which would occur in the absence of lysolipid.

A further aspect of the present invention is a liposome having a lipid bilayer membrane comprising phospholipids as the primary lipid source, and from 2 mole percent to 30 mole percent lysolipid.

A further aspect of the present invention is a method for preparing an active agent for hyperthermic administration. The active agent is entrapped in a liposome having a lipid bilayer membrane comprising phospholipids as the primary lipid source, and from 1 to 30% lysolipid.

A further aspect of the present invention is a liposomal preparation comprising a plurality of liposomes as described above.

A further aspect of the present invention is a method of making liposomes containing an active agent in the liposome interior space. A phospholipid film containing lysolipid is first prepared, and then hydrated with an aqueous preparation containing the active agent and an equilibrating amount of lysolipid monomer. Lysolipid is contained in the liposome membrane in an amount sufficient to increase the percentage of active agent released at the phase transition temperature of the liposome membrane, compared to that which would occur in the absence of the lysolipid.

DETAILED DESCRIPTION OF THE INVENTION

Figure 1:
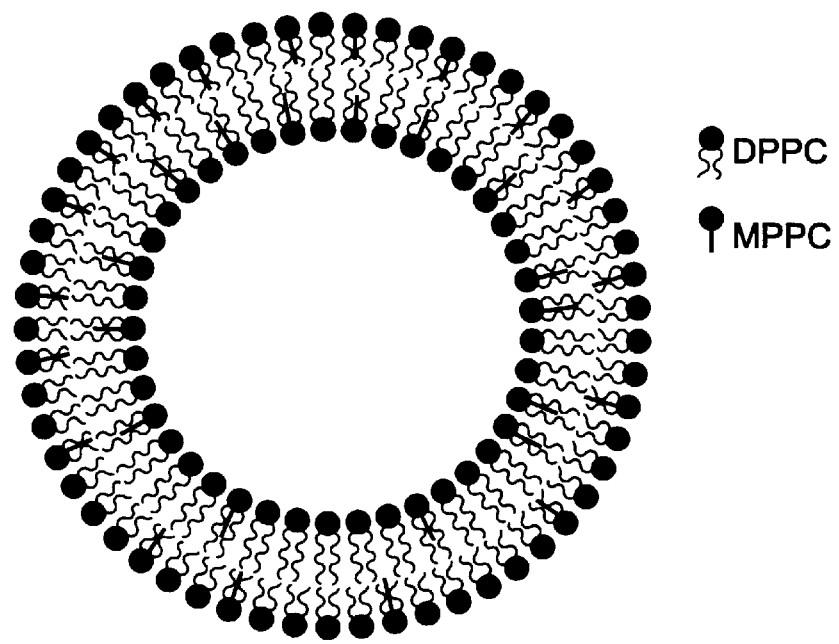
FIG. 1 schematically represents a liposome having a bilayer membrane containing dipalmitoylphosphatidylcholine (DPPC) as a phospholipid and monopalmitoylphosphatidylcholine (MPPC) as a lysolipid. The orientation of the lysolipid monomers and their presence in both the inner and outer layers of the lipid bilayer is indicated.

The present invention provides liposomes that are sensitive to alterations in the temperature of the surrounding environment. The temperature-sensitivity of such liposomes allows the release of compounds entrapped within the interior aqueous space of the liposome, and/or the release of compounds associated with the lipid bilayer, at a target site that is either heated (as in the clinical procedure of hyperthermia) or that is at an intrinsically higher temperature than the rest of the body (as in inflammation). Liposome bilayers of the present invention include (in addition to a primary or main lipid component) lysolipid, or another surface active agent(s). The inclusion of lysolipid or another surface active agent in the liposome bilayer enhances the release of compounds when the liposome temperature reaches the gel-to-liquid crystalline phase transition temperature of the primary lipid component. The presence of the lysolipid (or other surface active agent) also causes the liposome to release the drug at a slightly lower temperature than that achieved with liposomes composed solely of phospholipids. Liposomes of the present invention are particularly useful in drug delivery, where the liposome contains a compound to be delivered to a preselected target site in a subject's body. The target site is either artificially heated (hyperthermia) so that it is at or above the gel-to-liquid crystalline phase transition temperature, or the target site may be at a higher temperature than non-targeted sites in the body due to natural causes (e.g., inflammation), where that temperature is at or above the gel-to-liquid crystalline phase transition temperature of the liposome utilized.

When liposomes are incubated for several minutes at temperatures in the region of the gel-to-liquid crystalline phase transition temperature (Tc) of the primary lipid composing the liposome, the liposome bilayer becomes permeable and releases solutes entrapped within the liposome into the surrounding solution. The clinical use of hyperthermia with such thermally-sensitive liposomes has been proposed. See, e.g., Yatvin et al., Science 202:1290 (1978).

U.S. Pat. No. 5,094,854 (Ogawa et al.) discloses liposomes in which the osmotic pressure of the drug-containing solution entrapped in liposomes is 1.2–2.5 times higher than that of the body fluid of warm-blooded animals. The temperature range in which the liposome membrane becomes permeable to material release is stated to be in the range of 40° C. to 45° C.

U.S. Pat. No. 5,720,976 (Kim et al.) discloses the use of a copolymer of N-isopropylacrylamide/octadecylacrylate/acrylic acid to coat the liposomal surface to effect the release of agents contained within the liposome. Release of the entrapped agent occurs at temperatures above 28° C. (well below average human temperature).

Methods of heating a subject's body for therapeutic purposes or to assist in the delivery of therapeutic or diagnostic agents are known in the art. Hyperthermia consists of heating diseased sites, such as solid tumors, to temperatures higher than the physiological temperature (e.g., from about 38° C. to about 45° C.), and is currently used mainly as an adjunct to radiation therapy (Bates and Mc Killop Cancer Res. 46:5477 (1986); Herman, Cancer Res. 43, 511 (1983)).

As used herein, the term "hyperthermia" refers to the elevation of the temperature of a subject's body, or a part of a subject's body, compared to the normal temperature of the subject. Such elevation may be the result of a natural process (such as inflammation) or artificially induced for therapeutic or diagnostic purposes. In mammals, a normal body temperature is ordinarily maintained due to the thermoregulatory center in the anterior hypothalamus, which acts to balance heat production by body tissues with heat loss. "Hyperthermia" refers to the elevation of body temperature above the hypothalamic set point due to insufficient heat dissipation. In contrast to hyperthermia, "fever" refers to an elevation of body temperature due to a change in the thermoregulatory center. The overall mean oral temperature for a healthy human aged 18–40 years is 36.8±0.4° C. (98.2±0.7° F.). See, e.g., Harrison's Principles of Internal Medicine (Fauci et al., Eds.) 14$^{th}$ Edition, McGraw-Hill, New York, p. 84 (1998).

The use of hyperthermia with thermally-sensitive liposomes has been proposed, for example, for the treatment of tumors (Yatvin et al., Science 202:1290 (1978)). Using localized hyperthermia and thermally-sensitive liposomes to target anti-neoplastic agents to tumor sites in a subject acts to decrease undesirable side effects of the agent, and to enhance therapeutic results. However, the efficacy of liposomes targeted to diseased sites by hyperthermia depends on the stability of the liposome in the blood stream (when liposomes are administered to the circulatory system), and on the amount of active agent released by the liposome at the target site. For example, liposomes described by Yatvin et al, Science 202:1290 (1978) released only a portion of the drug carried by the liposome at hyperthermic temperatures.

As used herein, "hyperthermic administration" of an active agent refers to its administration in conjunction with the use of clinical hyperthermia in the subject at a preselected target site, to deliver a larger amount of active agent to the target site compared to that which would result from the administration of the active agent in the absence of hyperthermia.

Liposomes of the present invention comprise a lipid possessing a gel-to-liquid crystalline transition temperature in the hyperthermic range (e.g., the range of from approximately 38° C. to approximately 45° C.). Preferred are phospholipids with a phase-transition temperature of from about 38° C. to about 45° C., and more preferred are phospholipids whose acyl groups are saturated. A particularly preferred phospholipid is dipalmitoylphosphatidylcholine (DPPC). DPPC is a common saturated chain (C16) phospholipid with a bilayer transition of 41.5° C. (Blume, Biochemistry 22:5436 (1983); Albon and Sturtevant, Proc. Natl. Acad. Sci. USA 75:2258 (1978)). Thermosensitive liposomes containing DPPC and other lipids that have a similar or higher transition temperature, and that mix ideally with DPPC (such 1,2-Dipalmitoyl-sn-Glycero-3-[Phospho-rac-(1-glycerol)] (DPPG) (Tc=41.5° C.) and 1,2-Distearoyl-sn-Glycero-3-Phosphocholine (DSPC) (Tc=55.1° C.)) have been studied. Kastumi Iga et al, Intl. J. Pharmaceutics, 57:241 (1989); Bassett et al, J. Urology, 135:612 (1985); Gaber et al, Pharmacol. Res. 12:1407 (1995). Thermosensitive liposomes containing DPPC and cholesterol have also been described. Demel and De Kruyff, Biochim. Biophys. Acta. 457:109 (1976).

As used herein, the "primary lipid" in a liposome bilayer is that which is the main lipid component of liposome bilayer material. Thus, in a liposome bilayer composed of 70 mole % phospholipid and 30 mole % lysolipid, the phospholipid is the primary lipid.

Liposomes of the present invention incorporate a relatively-water soluble surface active agent, such as a lysolipid, into a bilayer composed primarily of a relatively water-insoluble molecule, such as a di-chain phospholipid (e.g., DPPC). Incorporation of the surface active agent in the gel phase of the primary lipid component enhances the release of contents from the resulting liposome when heated to the gel-liquid crystalline phase transition temperature of the primary lipid. Preferred surface active agents are lysolipids, and a particularly preferred surface active agent is monopalmitoylphosphatidylcholine (MPPC). Suitable surface-active agents are those that are compatible with the primary lipid of the bilayer, and that desorb when the lipid melts to the liquid phase. Additional suitable surface-active agents for use in phospholipid bilayers include palmitoyl alcohols, stearoyl alcohols, palmitoyl, stearoyl, polyethylene glycol, glyceryl monopalmitate, glyceryl monooleate, ceramides, PEG-ceramides, and therapeutic lipids. Therapeutic lipids include, for example, C-18 ether linked lyso-phoshpatidylchohline.

A preferred liposome of the present invention incorporates a bilayer-compatible lysolipid in a phospholipid bilayer, the lysolipid present in the bilayer at a concentration sufficient to enhance the release of contents (e.g., active agent or therapeutic agent) from the liposome, compared to the release of contents that would be achieved using a liposome composed of only lipid alone (i.e., without lysolipid). The contents may be contained within the interior of the liposome or in the liposome membrane. By "enhanced release", it is meant that either (a) that a greater percentage of contents is released at a given temperature, compared to the amount of contents released at that temperature by a lipsome with a bilayer composed of phospholipid only; or (b) the contents entrapped in the interior of the liposome are released at a lower temperature than the temperature at which release of contents would occur using a lipsome with a bilayer composed of phospholipid only.

The present invention provides liposomes that release entrapped contents at temperatures that can be achieved in clinical settings using mild hyperthermia. The present invention provides liposomes (THERMOSOMES™) that are highly stable at body temperature (37° C.) but that become unstable and show enhanced release of entrapped compounds at temperatures beyond about 39° C. This temperature range is a few degrees below that of many previous liposomal formulations that only showed significant release at temperatures greater than 42° C. Additionally, the present liposomal formulation's combination of lipid and compatible lysolipid provides a lipid/lysolipid mixture with a slightly lower gel-to-liquid crystalline transition temperature compared to that of pure lipid alone, yet the gel-to-liquid crystalline transition temperature is not broadened by the inclusion of a lysolipid.

A preferred liposome of the present invention has a bilayer composed primarily of phospholipid, and containing lysolipid in an amount that decreases the gel-to-liquid crystalline phase transition temperature of the bilayer, compared to a bilayer composed of phospholipid alone. A particularly preferred liposome of the present invention comprises a DPPC as the primary phospholipid and MPPC as the lysolipid, where the ratio of DPPC:MPPC is from about 99:1, 98:2, 97:3, 96:4, 95:5, 90:10, to about 80:20, 75:25, 70:30, 65:35, 60:40, or even 51:49 (by molar ratio).

The present invention provides a new system for delivering active agents in a lipid carrier, wherein active agents are released from the carrier over a narrow temperature range. Local heating of target sites to mildly hyperthermic temperatures (i.e., 39° C. to 41° C.) allows preferential delivery of the active agent to a diseased site. The present liposomes are suited for use in combination with hyperthermia to target active agents to disease sites, compared to conventional liposomes that only release active agents slowly and that are not thermosensitive, or compared to thermosensitive liposomes that do not release active agents unitl reaching temperatures of 42° C. or above.

While not wishing to be held to any single theory of action, the present inventors believe that the mechanism whereby lysolipids (or other surface active agents) enhance the release of contents from liposomes composed primarily of phospholipid is related to the way in which the lysolipid is mostly ideally mixed in the mixed gel phase bilayer, but creates defects at the microstructural level (microdomain boundaries) as it desorbs from the membrane upon bilayer melting at the primary acyl chain transition temperature (i.e., at the transition temperature of the primary bilayer lipid). The inclusion of a surface active agent such as a lysolipid lowers the phase transition temperature of a phospholipid membrane, compared to the phase transition temperature of a membrane composed solely of the phospholipid. In a liposome composed of DPPC and MPPC, the phase transition temperature is lowered depending on the amount of MPPC incorporated into the gel phase bilayer; the reduction of phase transition temperature that can be achieved is limited by the amount of MPPC that can be stably contained in the bilayer. Membranes composed of DPPC can stably contain from 1 mol % MPPC, up to about 20 mole % MPPC, 30% mole % MPPC, 40 mol % MPPC, or even 50 mol % MPPC, depending on other conditions such as the active agent contained within the liposome.

In liposome bilayers containing phospholipid and a surface active agent such as a lysolipid, it is preferable that the surface active agent be contained in both layers of the bilayer. This concept is illustrated in FIG. 1, which schematically represents a liposome composed of DPPC and MPPC. The molecules of MPPC are present in both the exterior and the interior layer of the liposome membrane bilayer. In a liposome containing surface active agent in only one layer of the bilayer, redistribution of the surface active agent to both layers of the bilayer will occur over time at temperatures above the gel transition temperature (e.g., in the liquid crystalline phase).

Figure 11A:
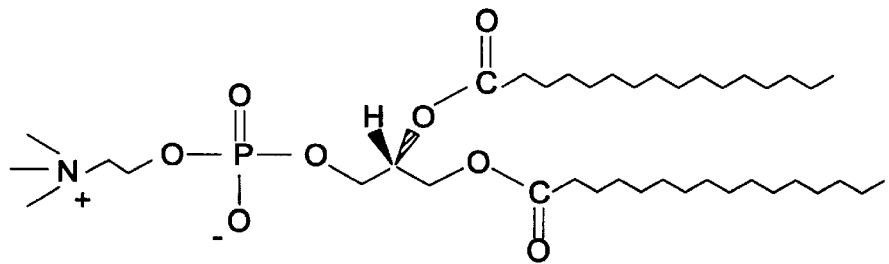
FIG. 11A shows the chemical structure of 1,2-Dipalmitoyl-sn-Glycero-3-Phosphocholine (DPPC).
Figure 11B:
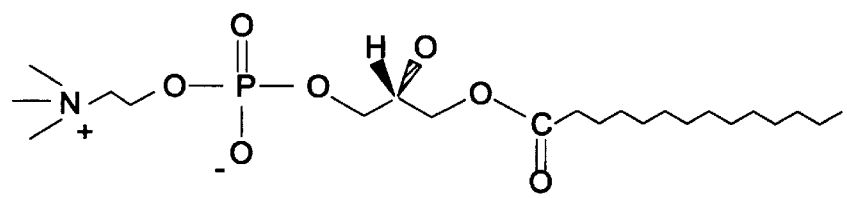
FIG. 11B shows the chemical structure of 1-Palmitoyl-2-Hydoxy-sn-Glycero-3-Phosphocholine (MPPC).

Phase compatibility of the two (or more) components of the present invention affects the processing and stability of the lipid bilayer structure. In liposomes composed primarily of DPPC (a di-chain phospholipid), to maximize compatibility and preserve the narrow melting range of the main phospholipid, a preferred lysolipid is MPPC because it is identical to the di-chain phospholipid except that it possesses only one acyl chain (FIGS. 11A and 11B). The present inventors discovered that inclusion of this bilayer-compatible lysolipid in low concentrations (preferably 2–20 mol %), makes liposomes composed primarily of DPPC more "leaky" at the point at which the primary lipid begins to melt (i.e., the solidus line of the main phase transition), compared to liposomes composed of DPPC alone. While not wishing to be held to a single explanation, the present inventors believe that gel phase bilayers are composed of microcrystalline domains; as the temperature approaches the gel-to-liquid crystalline phase transition of the lipid bilayer, membrane permeability to the entrapped drug increases at the grain boundaries of the microstructure. At the transition temperature, desorption of the lysolipid dissolved in the gel phase microstructure enhances the membrane permeability. An additional benefit of incorporating a compatible molecule in the liposome bilayer is that the phase transition temperature of the primary lipid is not broadened, but is lowered by about a degree or more (depending on the lysolipid concentration in the bilayer).

The process of forming the mixed component liposomes of the present invention involves preparation of gel phase liposomes containing a phospholipid, an appropriate surface active agent (such as lysolipid), and the active agent of interest. Other phase compatible components such as DSPE-PEG can optionally be included, as discussed further below. The composition contains a percentage of lysolipid such that the surface active agent does not destabilize the membrane at processing temperatures where the bilayer is in the liquid phase, nor at physiological temperatures where the bilayer is in the gel phase. The bilayer becomes unstable and permeable at temperatures just above normal human body temperature, and rapidly releases entrapped material from the liposome interior.

Liposomes according to the present invention may be prepared by any of a variety of techniques that are known in the art. See, e.g., U.S. Pat. No. 4,235,871; Published PCT applications WO 96/14057; New RRC, *Liposomes: A practical approach*, IRL Press, Oxford (1990), pages 33–104; Lasic D D, *Liposomes from physics to applications*, Elsevier Science Publishers, Amsterdam, 1993; *Liposomes*, Marcel Dekker, Inc., New York (1983). Entrapment of an active agent within liposomes of the present invention may also be carried out using any conventional method in the art. In preparing liposome compositions of the present invention, stabilizers such as antioxidants and other additives may be used as long as they do not interfere with the purpose of the invention.

The amount of surface active agent (such as lysolipid) included in liposomes of the present invention is not sufficient to destabilize the membrane in the liquid phase that occurs during processing of the liposomes (prior to cooling to produce the gel phase product). In producing liposomes according to the present invention, it is preferable during processing of the liquid phase membranes to maintain a concentration of surface active agent monomer both inside and outside the liposome, to avoid a concentration gradient that would deplete the lysolipid concentration in the membrane. This can be achieved by preparing the liposomal suspension from a premixed mixture in an aqueous medium containing sufficient amount of surface active agent in monomeric form, (e.g., at the critical micelle concentration (CMC) of the surface active agent).

A method of preparing a liposomal formulation according to the present invention comprises mixing the bilayer components in the appropriate proportions in a suitable organic solvent, as is known in the art. The solvent is then evaporated to form a dried lipid film. The film is rehydrated (at temperatures above the phase transition temperature of the lipid mixture) using an aqueous solution containing an equilibrating amount of the surface active agent and a desired active agent. The liposomes formed after rehydration can be extruded to form liposomes of a desired size, as is known in the art. For example, where liposomes composed of 80:20 DPPC:MPPC are produced, rehydration is carried out at a temperature above the phase transition temperature of this particular lipid mixture (above 39° C.). The aqueous solution used to rehydrate the lipid film comprises an equilibrating amount of lysolipid monomers (e.g., a concentration equal to the Critical Micelle Concentration of MPPC).

Conventional liposomes suffer from a relatively short half life in the blood circulation due to their rapid uptake by macrophages of the liver and spleen (organs of the reticuloendothelial system or RES), and therefore do not accumulate in leaky tumor tissue. Liposome preparations have been devised which avoid rapid RES uptake and which have increased circulation times. STEALTH® liposomes (Sequus Inc., Menlo Park Calif.) include polyethyleneglycol (PEG)-grafted lipids at about 5 mol % in the lipid bilayer. See, e.g., Allen, *UCLA Symposium on Molecular and Cellular Biology*, 89:405 (1989); Allen et al., *Biochim. Biophys. Acta* 1066:29 (1991); Klibanov et al., *FEBS Letters* 268:235 (1990); Needham et al., *Biochim. Biophys. Acta* 1108:40 (1992); Papahadjopoulos et al., *Proc. Natl. Acad. Sci. USA* 88:11460 (1991); Wu et al., *Cancer Research* 53:3765 (1993); Klibanov and Huang, *J. Liposome Research* 2:321 (1992); Lasic and Martin, Stealth Liposomes, In: Pharmacology and Toxicology, CRC Press, Boca Raton, Fla. (1995). See also U.S. Pat. No. 5,225,212 to Martin et al.; U.S. Pat. No. 5,395,619 to Zalipsky et al. regarding liposomes containing polymer grafted lipids in the vesicle membrane. The presence of polymers on the exterior liposome surface decreases the uptake of liposomes by the organs of the RES.

Liposomes of the present invention may be formulated to include polymer-grafted lipids, as is known in the art, to decrease liposome uptake by the RES and thus increase the circulation time of the liposomes. Suitable polymers include hydrophilic polymers such as polyethylene glycol, polylactic acid, polyglycolic acid, copolymers of polylactic acid and polyglycolic acid, and polyvinyl alcohols.

Active Agents

As used herein, an active agent 'in the interior' or 'entrapped within' the liposome is that which contained in the interior space of the liposome, compared to that partitioned into the lipid bilayer and contained within the vesicle membrane itself. As used herein, an active agent 'within' or 'entrapped within' the lipid bilayer of a liposome is carried as a part of the lipid bilayer, as opposed to being contained in the interior space of the liposome. Active agents may be in any form suitable for use in liposomes, as is known in the art, including but not limited to aqueous solutions of active agents. Aqueous solutions of active agents within liposomes of the present invention may be at the same osmotic pressure as that of the body fluid of the intended subject, or at an increased osmotic pressure (see U.S. Pat. No. 5,094,854); the aqueous solutions may also contain some precipitated active agent, as is known in the art. A preferred active agent for encapsulation in the interior of the liposome is any water soluble, weak base agent.

The incorporation of certain active agents (such as some anesthetics) in liposomes of the present invention may additionally alter (enhance or inhibit) the release of contents from the liposome, or alter the transition temperature of the liposome, compared to that which would be seen in a similar liposome that did not contain the active agent.

The administration of antineoplastic or antitumor drugs such as doxorubicin, cisplatin and methotrexate using thermosensitive liposomes in combination with hyperthermia at the desired target site has been reported. See, e.g., Magin and Weinstein In: *Liposome Technology*, Vol. 3, (Gregoriadis, G., ed.) p. 137, CRC Press, Boca Raton, Fla. (1993); Gaber et al., *Intl. J. Radiation Oncology, Biol. Physics,* 36(5):1177 (1996).

Active agents suitable for use in the present invention include therapeutic drugs and pharmacologically active agents, nutritional molecules, cosmetic agents, diagnostic agents and contrast agents for imaging. As used herein, active agent includes pharmacologically acceptable salts of active agents. Suitable therapeutic agents include, for example, antineoplastics, antitumor agents, antibiotics, antifungals, anti-inflammatory agents, immunosuppressive agents, anti-infective agents, antivirals, anthelminthic, and antiparasitic compounds. Methods of preparing lipophilic drug derivatives which are suitable for liposome formulation are known in the art (see e.g., U.S. Pat. No. 5,534,499 to Ansell, describing covalent attachment of therapeutic agents to a fatty acid chain of a phospholipid).

In treating tumors or neoplastic growths, suitable compounds may include anthracycline antibiotics (such as doxorubicin, daunorubicin, carinomycin, N-acetyladriamycin, rubidazone, 5-imidodaunomycin, N30 acetyldaunomycin, and epirubicin) and plant alkaloids (such as vincristine, vinblastine, etoposide, ellipticine and camptothecin). Other suitable agents include paclitaxel (TAXOL®; a diterpenes isolated from the bark of the yew tree and representative of a new class of therapeutic agents having a taxane ring structure) and docetaxol (taxotere); mitotane, cisplatin, and phenesterine.

Anti-inflammatory therapeutic agents suitable for use in the present invention include steroids and non-steroidal anti-inflammatory compounds, such as prednisone, methylprednisolone, paramethazone, 11-fludrocortisol, triamciniolone, betamethasone and dexamethasone, ibuprofen, piroxicam, beclomethasone; methotrexate, azaribine, etretinate, anthralin, psoralins; salicylates such as aspirin; and immunosuppresant agents such as cyclosporine. Antiinflammatory corticosteroids and the antiinflammatory and immunosuppressive agent cyclosporine are both highly lipophilic and are suited for use in the present invention.

Additional pharmacologic agents suitable for use in liposomes of the present invention include anesthetics (such as methoxyflurane, isoflurane, enflurane, halothane, and benzocaine); antiulceratives(such as cimetidine); antiseizure medications such as barbituates; azothioprine (an immunosuppressant and antirheumatic agent); and muscle relaxants (such as dantrolene and diazepam).

Imaging agents suitable for use in the present liposome preparations include ultrasound contrast agents, radiocontrast agents (such as radioisotopes or compounds containing radioisotopes, including iodo-octanes, halocarbons, and renograf in), or magnetic contrast agents (such as paramagnetic compounds).

Nutritional agents suitable for incorporation into liposomes of the present invention include flavoring compounds (e.g., citral, xylitol), amino acids, sugars, proteins, carbohydrates, vitamins and fat. Combinations of nutritional agents are also suitable.

Administration and Liposome Size

Liposomes of the present invention may be administered using methods that are known to those skilled in the art, including but not limited to delivery into the bloodstream of a subject or subcutaneous administration of liposomes. Where liposomes according to the present invention are used in conjunction with hyperthermia, the liposomes may be administered by any suitable means that results in delivery of the liposomes to the treatment site. For example, liposomes may be administered intravenously and thereby brought to the site of a tumor by the normal blood flow; heating of this site results in the liposomal membranes being heated to the phase transition temperature so that the liposomal contents are preferentially released at the site of the tumor.

Where treatment of a tumor or neoplasm is desired, effective delivery of a liposome-encapsulated active agent via the bloodstream requires that the liposome be able to penetrate the continuous (but "leaky") endothelial layer and underlying basement membrane surrounding the vessels supplying blood to a tumor. Liposomes of smaller sizes have been found to be more effective at extravasation into tumors through the endothelial cell barrier and underlying basement membrane which separates a capillary from tumor cells. See, e.g., U.S. Pat. No. 5,213,804 to Martin et al.

As used herein, "solid tumors" are those growing in an anatomical site other than the bloodstream (in contrast to blood-borne tumors such as leukemias) Solid tumors require the formation of small blood vessels and capillaries to nourish the growing tumor tissue.

In accordance with the present invention, the anti-tumor or anti-neoplastic agent of choice is entrapped within a liposome according to the present invention; the liposomes are formulated to be of a size known to penetrate the endothelial and basement membrane barriers. The resulting liposomal formulation can be administered parenterally to a subject in need of such treatment, preferably by intravenous administration. Tumors characterized by an acute increase in permeability of the vasculature in the region of tumor growth are particularly suited for treatment by the present methods. Administration of liposomes is followed by heating of the treatment site to a temperature that results in release of the liposomal contents.

Where site-specific treatment of inflammation is desired, effective liposome delivery of an active agent requires that the liposome have a long blood halflife, and be capable of penetrating the continuous endothelial cell layer and underlying basement membrane surrounding blood vessels adjacent to the site of inflammation. Liposomes of smaller sizes have been found to be more effective at extravasation through the endothelial cell barrier and into associated inflamed regions. See, e.g., U.S. Pat. No. 5,356,633 to Woodle et al. In accordance with the present invention, the anti-inflammatory agent of choice is entrapped within a liposome according to the present invention; the liposomes are formulated to be of a size known to penetrate the endothelial and basement membrane barriers. The resulting liposomal formulation can be administered parenterally to a subject in need of such treatment, preferably by intravenous administration. Inflamed regions characterized by an acute increase in permeability of the vasculature in the region of inflammation, and by a localized increase in temperature, are particularly suited for treatment by the present methods.

It will further be appreciated that the liposomes of the present invention may be utilized to deliver of anti-infective agents to sites of infection, via the bloodstream. The use of liposomes containing a vesicle-forming lipid derivatized with a hydrophilic polymer, and having sizes ranging between 0.07 and 0.2 microns, to deliver therapeutic agents to sites of infection is described in published PCT patent application WO 93/19738. In accordance with the present invention, the anti-infective agent of choice is entrapped within a liposome having a membrane according to the present invention, and the resulting liposomal formulation is administered parenterally to a subject, preferably by intravenous administration. If desired, localized hyperthermia may be induced at the site of infection to cause the preferential release of liposomal contents at that site.

The size of liposomes in a preparation may depend upon the active agent contained therein and/or the intended target. Liposomes of between 0.05 to 0.3 microns in diameter. have been reported as suitable for tumor administration (U.S. Pat. No. 5,527,528 to Allen et al.) Sizing of liposomes according to the present invention may be carried out according to methods known in the art, and taking into account the active agent contained therein and the effects desired (see, e.g., U.S. Pat. No. 5,225,212 to Martin et al; U.S. Pat. No. 5,527,528 to Allen et al). A preferred embodiment of the present invention is a liposome of less than 10 microns in diameter, or a liposome preparation containing a plurality liposomes of less than 10 microns in diameter. In a further preferred embodiment of the present invention, liposomes are from about 0.05 microns or about 0.1 microns in diameter, to about 0.3 microns or about 0.4 microns in diameter. Liposome preparations may contain liposomes of different sizes.

In another preferred embodiment of the present invention, liposomes are from about 50 nm, 100 nm, 120 nm, 130 nm, 140 nm or 150 nm, up to about 175 nm, 180 nm, 200 nm, 250 nm, 300 nm, 350 nm, 400 nm or 500 nm in diameter.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

In a further aspect of the present invention, liposomes are dispersed in physiological saline or PBS to provide an aqueous preparation of liposomes. The aqueous preparation may further include an equilibrating amount of the surface active agent contained in the liposome bilayer, to reduce or prevent loss of the surface active agent from the liposome bilayer into solution. Liposomes composed of DPPC:MPPC may be contained in physiological saline or PBS that contains from about 1 mmM to about 5 mM of MPPC monomer.

The amount of active agent to be entrapped within or carried by liposomes according to the present invention will vary depending on the therapeutic dose and the unit dose of the active agent, as will be apparent to one skilled in the art. In general, however, the preparation of liposomes of the present invention is designed so the the largest amount of active agent possible is carried by the liposome. Liposomes of the present invention may be of any type, however, LUVs are particularly preferred.

Assessing Release of Liposome Contents

Characterization of thermosensitive liposomes by the release of an entrapped fluorescent probe, 6-Carboxyfluorescein (CF), was reported in Merlin, *Eur. J. Cancer* 27(8): 1031 (1979). CF was entrapped into liposomes at a quenching concentration (50 mM); no fluorescence was observed for CF entrapped in the liposome. Intense fluorescence, however, developed upon release of the probe from liposomes due to dilution of the CF in the suspension. The amount of the probe released from the liposomes at various temperatures could thus be quantified based on fluorescence. Merlin, *Eur. J. Cancer.*, 27(8):1031 (1991), studied thermally sensitive liposomes encapsulating Doxorubicin (DX), and incorporated pegylated lipids in the bilayer to increase their circulation time in the blood stream compared to conventional thermosensitive liposomes. See also Maruyama et al., *Biochem. Biophys. Acta,* 1149:17 (1993)).

The examples which follow are set forth to illustrate the present invention, and are not to be construed as limiting thereof.

EXAMPLE 1

Preparation of Temperature—Sensitive Liposomes

DPPC liposomes containing varied molar concentrations of the lysolipid Monopalmitoylphosphatidylcholine (MPPC) were prepared and characterized. The aqueous fluorescent probe 6-Carboxyfluorescein (CF) was entrapped within the liposomes to act as a marker for membrane permeability change; CF was incorporated into the liposomes using methods known in the art (See, e.g., *Liposomes: A Practical Approach* (1990), Editor: R.R.C. New, IRL Press, Oxford, N.Y.). The liposome components were dissolved in chloroform (a suitable organic solvent), and the solvent was evaporated under vacuum at 45° C. using a rotavapor to form a uniform thin film of lipids on the inner walls of a round bottom flask. The lipid film was further dried under vacuum for 25 hours to ensure complete removal of traces of chloroform.

The lipid film was hydrated at 45° C. with an aqueous solution of 10 mM PBS (pH=7.4) containing 50 mM CF and 1 mM MPPC. For efficient hydration, a TEFLON® bead was used to gently etch the lipids in the presence of aqueous medium to form a cloudy suspension of multilamellar vesicles (MLVs). The MLVs thus formed had an average size of 700 nm and were extruded through a stack of two polycarbonate membrane filters of 0.1 micrometers under 300–400 psi pressure at 45° C. (i.e., above the gel-liquid crystalline temperature of the lipid or lipid mixture) as described in the method developed by Hope et al. (*Biochem. Biophys. Acta* 812:55–65 (1985)) to obtain Large Unilamellar Vesicles by Extrusion Technique (LUVETs) of the desired 140 nm size. The mean diameter of the vesicles was measured by Photon Correlation Spectrometer (PCS, Coulter, N4 plus) after each extrusion pass.

Figure 2:
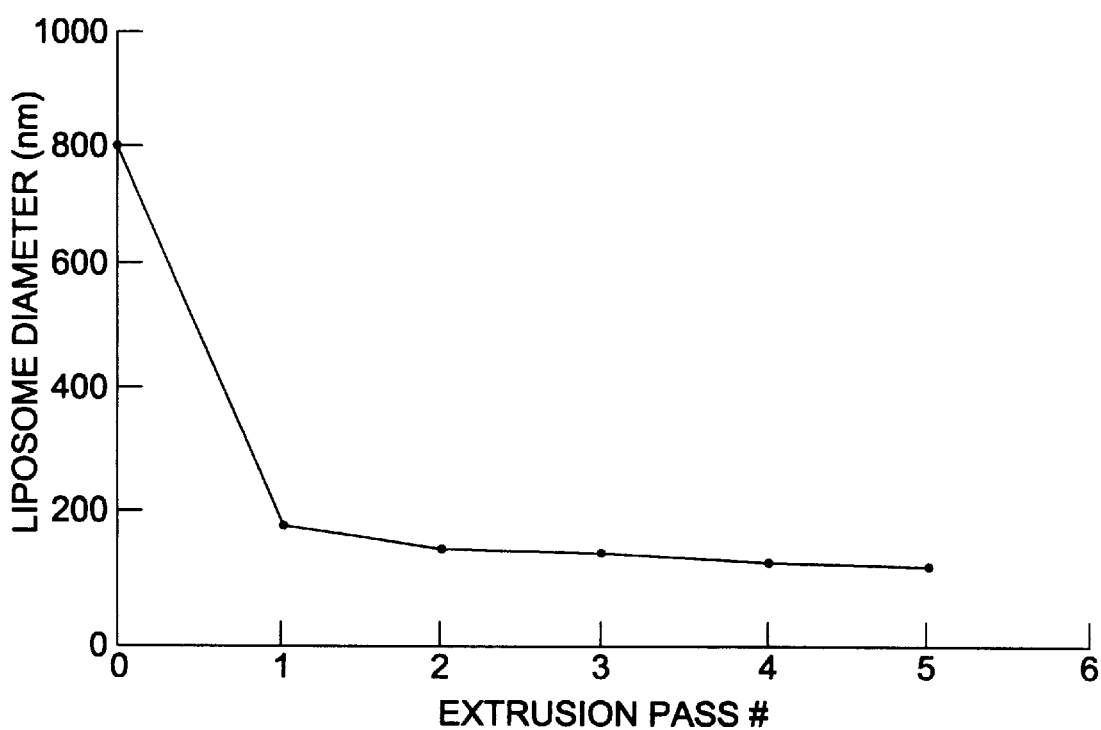
FIG. 2 graphs the effect of extrusion pass on the mean diameter of DPPC liposomes containing DPPC:MPPC (90:10). Multilamellar vesicles with an average size of 700 nm were extruded through a stack of two polycarbonate membranes of pore size 0.1 mM under a pressure of 300–400 psi at 45° C.

As shown in FIG. 2, the size of liposomes decreased with successive passes through the membrane and reached the minimum size after three passes.

EXAMPLE 2

Release of Liposomal Contents

The in vitro stability and thermosensitivity of the liposomal formulations prepared as described in Example 1 and containing various molar fractions of MPPC was assessed by measuring the percent release of entrapped water soluble fluorescent molecule, CF, from the aqueous interior of the vesicle to the surrounding solution as a function of incubation temperature (25–45° C.) in the presence of PBS. The fluorescence of CF entrapped in the liposomes was self quenched due to its high concentration, but upon release from the liposomes and dilution into the suspending medium, CF developed an intense fluorescence. After incubation, the fluorescence intensity of the samples was measured at excitation wavelength ($\lambda$ex)=470 nm and emission wavelength ($\lambda$em)=520 nm after suitable dilutions to determine the amount of CF released from the liposomes. The relative percent fluorescence intensity due to incubation at a particular temperature was calculated by comparison with the total release of entrapped material obtained after disruption of the liposome samples by adding 10% TritonX-100.

This experiment was carried out for liposomes composed of pure DPPC and for liposomes composed of DPPC:MPPC mixtures containing 2, 4, 6, 7, 8, 10 or 20 mol % MPPC, over the temperature range 20° C. to 45° C.

Figure 3:
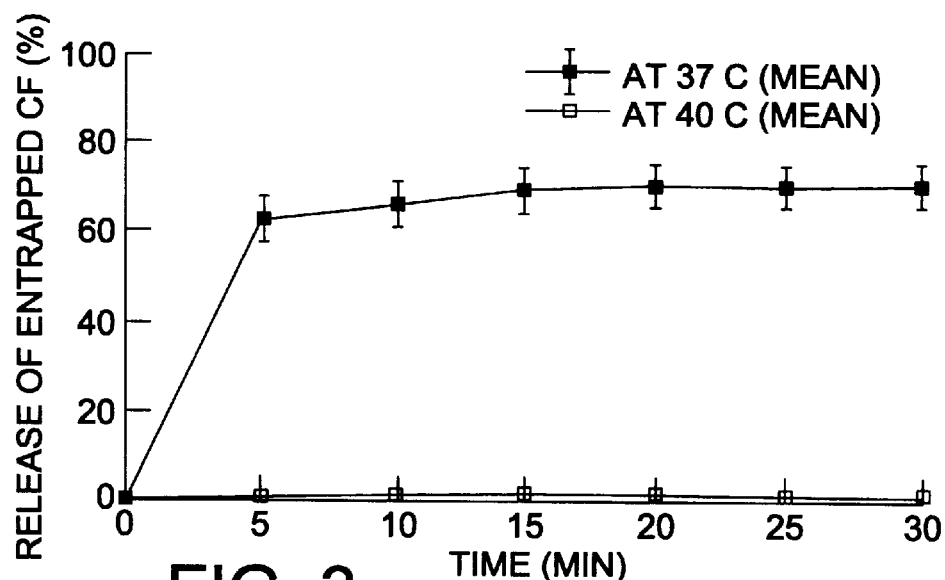
FIG. 3 graphs the release of 6-Carboxyfluorescein (CF) entrapped in liposomes composed of DPPC:MPPC (90:10), as a function of time in the presence of PBS at 37° (open circles) and 40° C. (closed squares).

The amount of entrapped CF released from liposomes of the present invention was measured as a function of time at physiological (37° C.) and hyperthermic (40° C.) temperatures. Liposomes were incubated in PBS for various time intervals and the release of CF was measured fluorimetrically at $\lambda$ex=470 nm and $\lambda$em=520 nm. Typical heating runs are shown in FIG. 3, for the 90:10 DPPC:MPPC composition. At 37° C. the percent release of CF was negligible. However, on incubation at 40° C., about 60% of the entrapped CF was released within five minutes; additional contents release only increased slightly upon further incubation at this temperature. Thus at a given temperature, most of the contents are released within the first five to ten minutes of heating.

Figure 4:
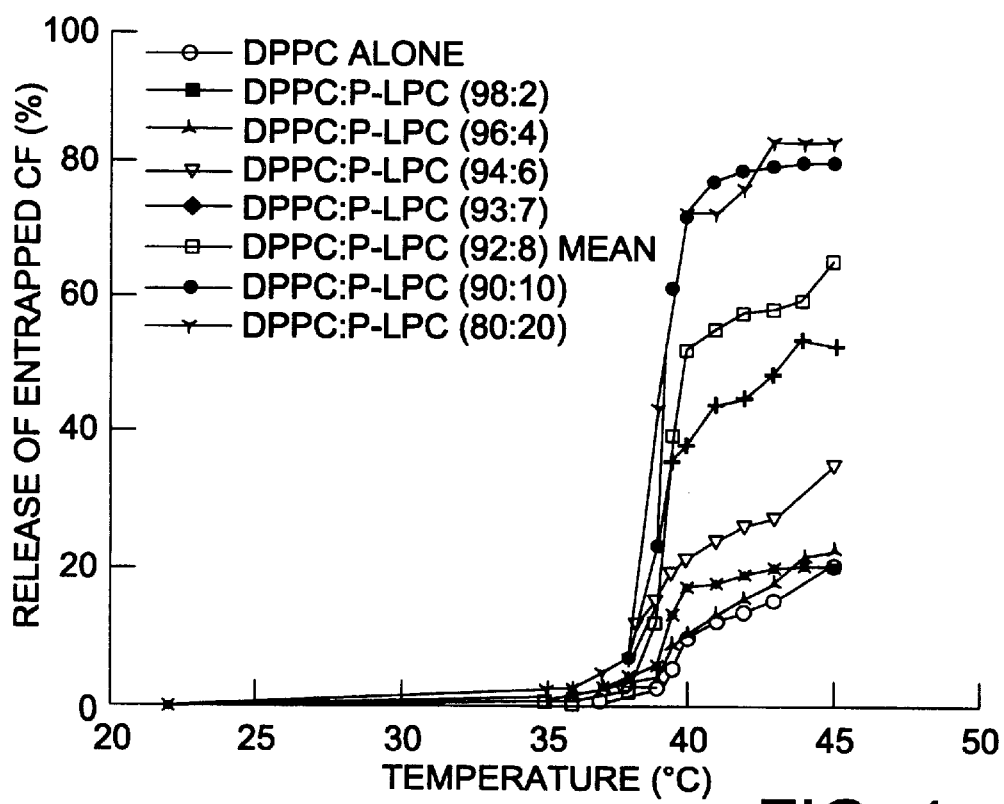
FIG. 4 graphs the release of CF from DPPC:MPPC liposomes of varied concentrations, at temperatures between 20° C. and 45° C. in the presence of 10 mM PBS (pH=7.4). Liposomes contained DPPC alone (open circles); DPPC:MPPC 98:2 (closed squares); DPPC:MPPC 96:4 (closed triangles ▲); DPPC:MPPC 94:6 (open triangles ▽); DPPC:MPPC 93:7 (closed diamonds); DPPC:MPPC 92:8 (open squares); DPPC:MPPC 90:10 (closed circles); DPPC:MPPC 80:20 (closed triangles ▼).

FIG. 4 shows the release of CF from liposomes incubated for five minutes at temperatures of 20° C. to 45° C. in the presence of 10 mM PBS (pH=7.4). Release of CF was measured fluorimetrically at $\lambda$ex=470 nm and $\lambda$em=520 nm. The percent of CF released was calculated by comparing the values obtained with those obtained after the total release of CF (achieved by the addition of Triton X-100 to the liposome sample to dissolve the liposomes and release all entrapped CF). Pure DPPC liposomes were stable up to 39.5° C. but became permeable near the transition temperature of the phospholipid, thus causing release of some of the CF. The amount of CF released from the pure DPPC liposome was, however, only about 20% of total contents. In contrast, with increasing concentrations of MPPC in the DPPC bilayers, liposomes showed an increasing release of CF, with maximum release occurring for the liposomes having bilayers containing 10 mol % and 20 mol % MPPC.

These results demonstrate that the incorporation of as little as 10 mol % of MPPC into the membranes of DPPC liposomes increases the amount of CF released by a factor of 4 (compared to the release that is seen for liposomes of DPPC alone), allowing release of up to 90% of the liposomal contents.

The temperature release profiles also show an additional benefit of incorporating MPPC into DPPC liposome membranes, in that the onset temperature for release is shifted to slightly lower temperatures, starting at approximately 38° C. for liposomes containing 10 mol % and 20 mol % MPPC. The release profile is sharp for these liposomes, and the maximum amount of CF is released after a rise in temperature of only a degree or so, i.e., at between 38.5° C. and 40° C. for the 10% MPPC liposomes.

These experiments demonstrate that the inclusion of MPPC in liposome bilayers made of DPPC increases the amount of contents released from the interior of the liposome, and shifts the temperature range over which release occurs into the range of 38.5° C.–40° C., which is the mild hyperthermic range.

In DPPC liposomes containing MPPC concentrations of more than 20 mol %, the liposomes became intrinsically unstable and therefore unable to retain entrapped material at temperatures above the lipid phase transition (i.e., in the liquid phase of the lipid bilayer that occurs during processing of liposomes). Such high concentrations of MPPC can also destabilize the gel phase bilayers at temperatures below the transition temperature. As demonstrated previously, the mechanical strength of membranes decreases as more and more MPPC is included (Needham et al., *Biophys. J.* 73:2615 (997)), and the bilayers eventually make a transition to a pure micelle suspension as the mole ratio of MPPC to phospholipid goes beyond 50 mol % (Zhelev et al., *Biophys. J.* (in press; 1998)). One preferred molar ratio for thermally sensitive liposomes is 90:10, DPPC:MPPC.

EXAMPLE 3

Figure 5A:
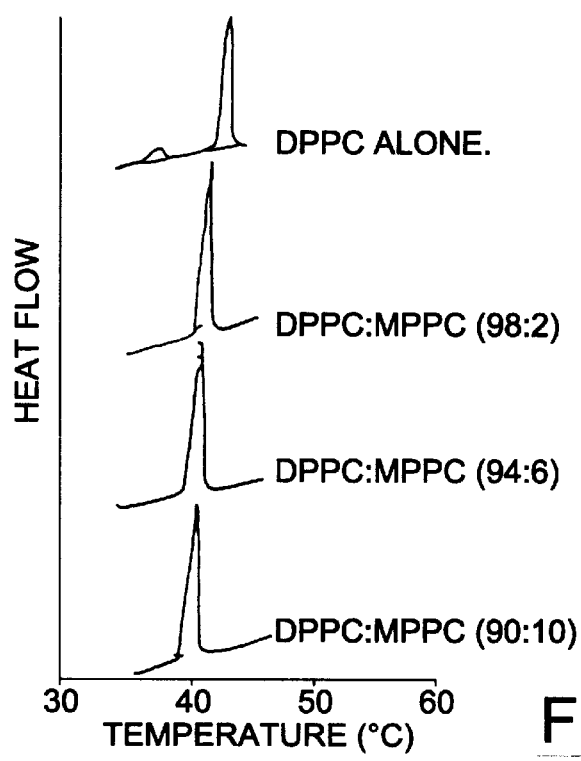
FIG. 5A provides heat flow thermograms showing the effect of varied MPPC concentration on the phase transition temperature (Tc) of DPPC liposomes. The Tc of lyophilized liposomal samples of DPPC containing MPPC (1–10 mol %) was measured by Differential Scanning Calorimetry (DSC) between 30° C.–45° C. with 2 C°/minute heating rate.
Figure 5B:
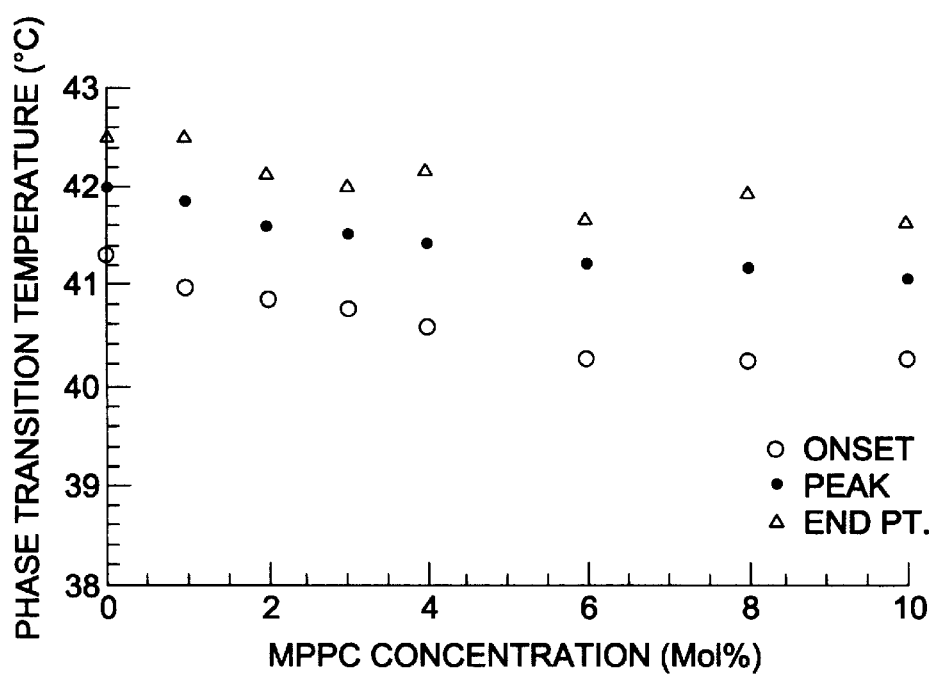
FIG. 5B graphs the effect of MPPC concentration on the phase transition temperature (Tc) of DPPC liposomes, as described above for FIG. 5A. The graph shows the start point of the transition (open circle); the peak in enthalpy (closed circle); and the end point of the transition (open triangle).

Phase Transition Behavior of DPPC/MPPC Mixtures and Correlations with Release Temperatures To investigate the biophysical mechanism involved in the permeability of the liposomes of the present invention, differential scanning calorimetric (DSC) studies were carried out to generate differential calorimetric thermograms for the present liposomes, to determine the phase transition temperature. These results were compared with the release versus temperature scans obtained from cumulative release profiles (shown in FIG. 4). FIGS. 5A and 5B show the heat flow thermograms for liposome preparations containing increasing concentrations of MPPC in DPPC bilayers. These thermograms show that the transition temperature remains unbroadened even though up to 10% of MPPC are included in the bilayer. At a higher level of resolution, FIG. 5B shows the change in the peak of the transition temperature from 41.9° C. to 41.04° C. as the MPPC composition is increased from zero to 10 mol % in DPPC bilayers. Also shown is the breadth of the transition, represented as the start and end point of the transition, i.e., the solidus and liquidus lines below and above the excess heat flow peak.

Figure 6A:
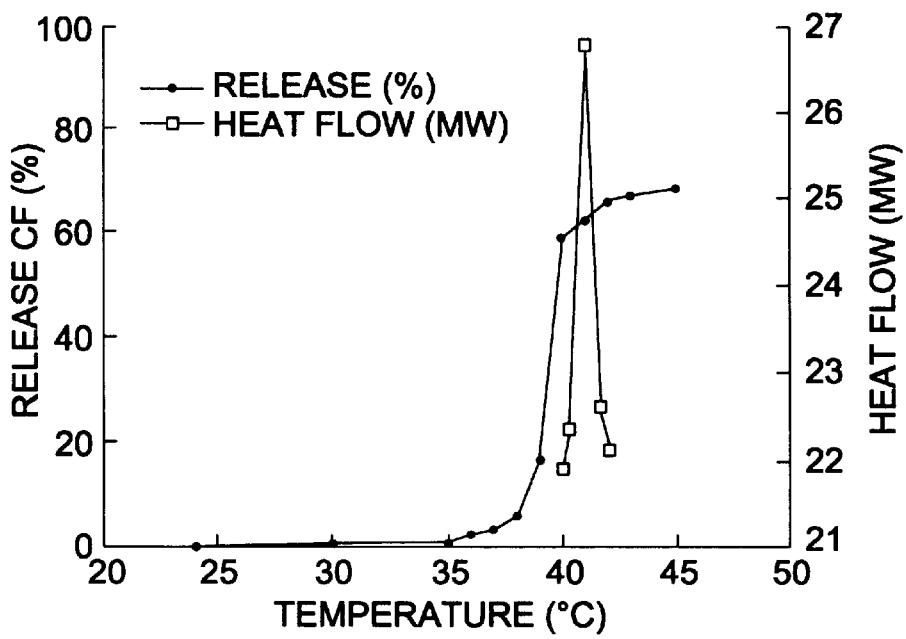
FIG. 6A compares the differential scanning calorimetric profile (excess heat flow; open squares) of liposomes (90:10 DPPC:MPPC) with the differential release profile (solid circles) for 6-Carboxyfluorescein (CF) release, as obtained from the cumulative release experiment described in FIG. 4.
Figure 6B:
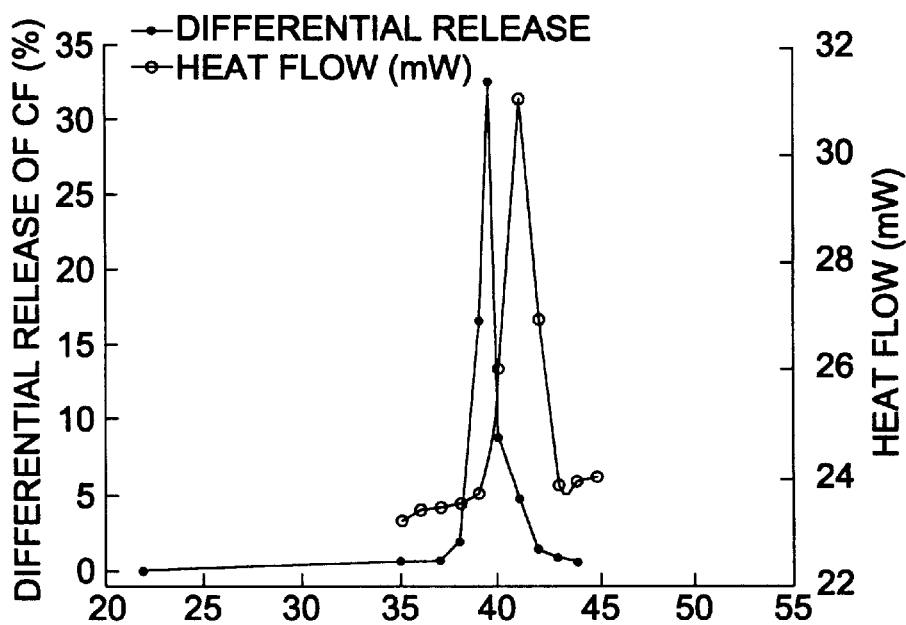
FIG. 6B graphs the differential release profile from 90:10 DPPC:MPPC liposomes, where open circles represent heat flow and solid circles represent differential release of CF over temperatures of from 25° C. to 45° C.

The differential scanning thermogram of liposomes of the present invention can be compared with the differential release profiles. FIG. 6A shows the cumulative release profile for CF release from the DPPC:MPPC 90:10 liposomes versus temperature, and the heat flow thermogram over the same temperature range. FIG. 6B shows the differential release, which highlights the sharpness of the release profile and the temperature at which maximum release occurs in relation to the heat flow thermogram. What is striking about this comparison is that that the peak release of contents obtained from the differential release profiles was 0.9° C. lower than the peak in the transition enthalpy obtained by DSC. The release of the entrapped material at the temperature prior to Tc can be attributed to the fact that the release is occurring at the 'solidus' line of the thermogram and not at the peak temperature. One explanation for such a behavior is that the release of entrapped material occurs as soon as the 'first defects' (melting defects) in the microdomain boundaries of the bilayer network appear; it is here that the lysolipid may exert its effects. While not wishing to be held to a single theory, the present inventors suspect that as the transition temperature is approached the first parts of the microstructure that melt are at the grain boundaries of the solid membrane. When surrounded by a lysolipid-free aqueous phase, the lysolipid is trapped in the gel phase but can desorb when the membrane begins to melt; as it does so it enhances the defect permeability and the contents are released more effectively than in liposomes of pure lipid alone.

EXAMPLE 4

Entrapment and Release of Doxorubicin

Doxorubicin (DX) was entrapped into the inner aqueous volumes of liposomes of the present invention (DPPC:MPPC 90:10) using the pH gradient-driven encapsulation protocol (L. D. Mayer et al (1989) *Cancer Res.*, 42:4734.). Briefly, a lipid composition of 90:10 DPPC:MPPC was dissolved in chloroform and the solvent was evaporated under vacuum at 45° C. using a rotavapor. The lipid film obtained after further drying in the vacuum desiccator overnight was hydrated with 300 mM citrate buffer (pH 4.00) and the multilamellar vesicles formed were subjected to seven freeze-and-thaw cycles. The resulting suspension was extruded through two polycarbonate membrane filters of pore size 0.1 $\mu$M at 50° C. using 300–400 psi pressure. The extruded liposomes were allowed to cool to room temperature and the pH was raised to 7.5–8.0 using 0.5 M $Na_2CO_3$ solution.

The extruded liposomes were incubated at 60° C. for five minutes before adding pre-heated DX to the suspension. Samples were further heated for 10 minutes at 60° C. with intermittent vortexing. The unentrapped drug was removed by mini-column centrifugation using Sephadex G-50 gel.

Figure 7:
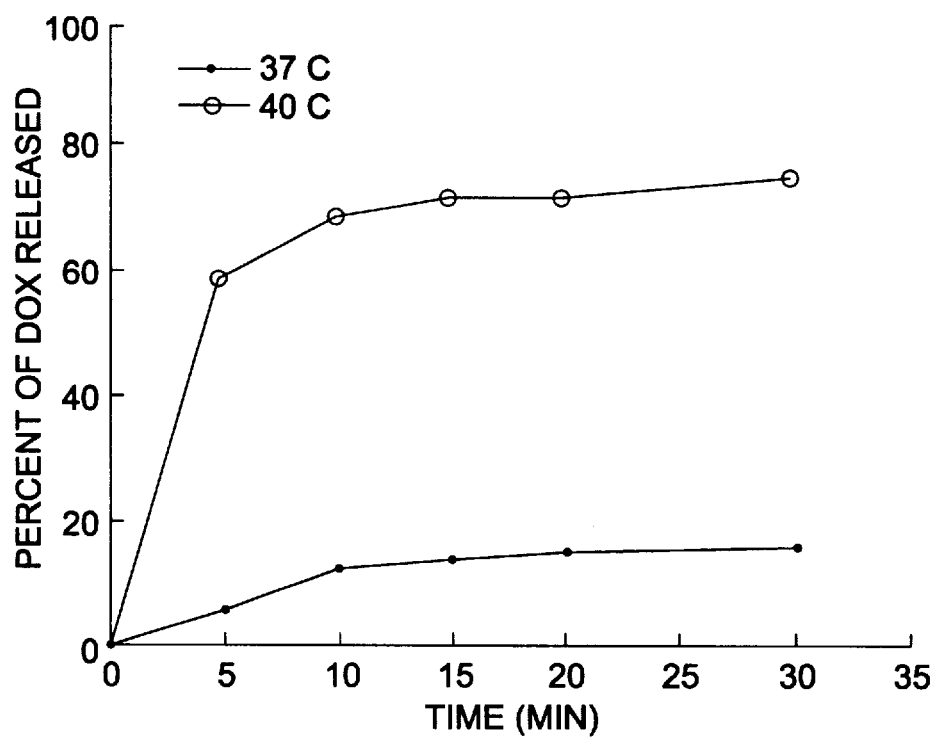
FIG. 7 graphs the release of entrapped Doxorubicin (DX) from liposomes (90:10 DPPC:MPPC) as a function of time at 37° C. (solid circles) and 40° C. (open circles) in the presence of PBS.

The DX entrapped liposomes were characterized by the release of DX from liposomes in the presence of PBS as a function of time at 37° and 40° C., as well as by the cumulative release profiles of entrapped DX from the liposomes at various temperatures between 25°–45° C. FIG. 7 represents the release of entrapped DX from liposomes as a function of time at 37° C. and 40° C. the liposomes were incubated at 37° and 40° C. for 30 minutes and the fluorescence intensity of the released DX was measured after suitable dilutions at $\lambda ex=470$ nm and $\lambda em=585$ nm. The percent release was calculated by comparing these values with values for the total release of 6-Carboxyfluorescein (obtained by the addition of Triton X-100 to the liposome sample). As can be seen from FIG. 7, about 14% of the DX was released at 37° C. after 30 minutes of incubation, whereas 73% of the drug was released at 40° C. after 30 minutes.

Figure 8:
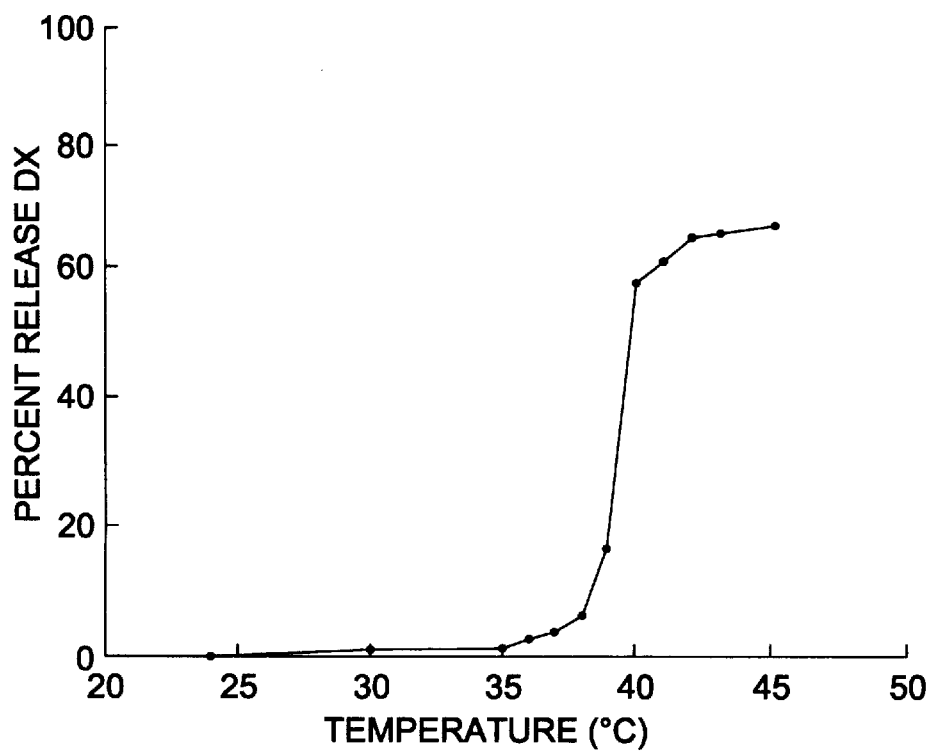
FIG. 8 graphs the cumulative release profiles of entrapped DX from liposomes composed of 90:10 DPPC:MPPC, incubated at temperatures of between 25° C. and 45° C. for five minutes in the presence of PBS.

As with the above studies (Examples 1–3) using CF, the cumulative release of DX entrapped in DPPC:MPPC 90:10 liposomes was measured by incubating the samples at various temperatures between 25°–45° C. for five minutes and measuring the released DX fluorimetrically, as shown in FIG. 8. The results showed about 23% release of DX up to 39° C. and reached 65% release at 40° C.

EXAMPLE 5

Inclusion of PEG in Liposome Bilayers

Liposomes of the present invention were modified to render them less recognizable by the RES, thereby enhancing their half life in the blood circulation.

Figure 11C:
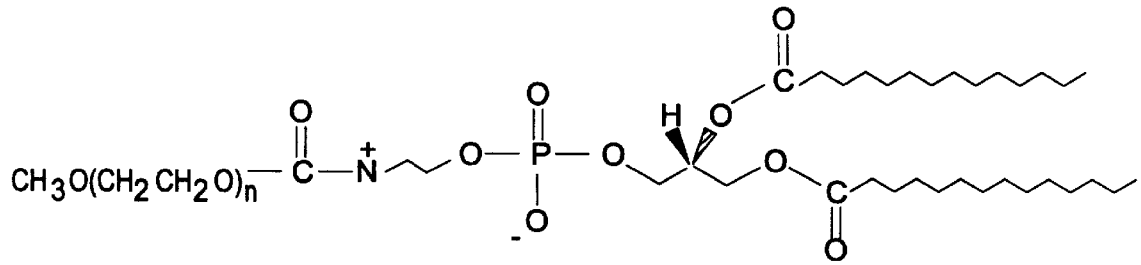
FIG. 11C shows the chemical structure of 1,2-Distearoyl-sn-Glycero-3-Phosphoethanolamine-N-[Poly(ethyleneglycol) 2000] (DSPE-PEG2000).

The surface of liposomes containing DPPC:MPPC 90:10 was modified by incorporating 5 mol % of DSPE-PEG (M.W. 2000) (FIG. 11C) in the liposome composition. Thus, the modified composition of these liposomes was DPPC: MPPC: DSPE-PEG-2000 (85.935:9.545:4.520).

EXAMPLE 6

Influence of Biological Fluids on Release of Liposome Contents

Surface-modified liposomes as described in Example 5 were characterized by studying the release profiles of CF entrapped in the aqueous interior liposomal region in the presence of either PBS or 50% bovine serum. The fluorescent intensity of released CF was measured at $\lambda ex=470$ nm and $\lambda em=520$ nm, and the percent release was calculated as described in Example 3.

Figure 9A:
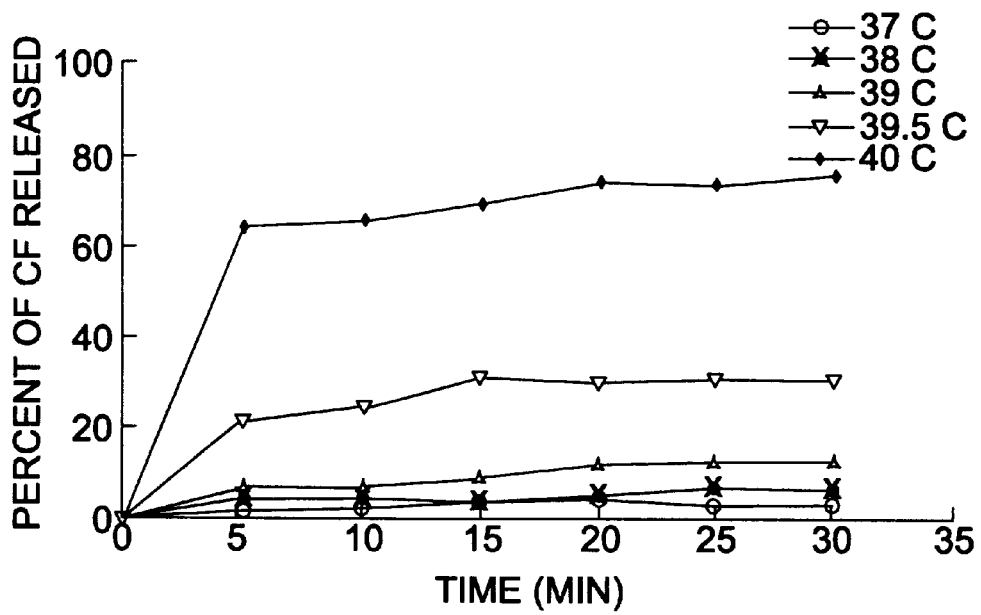
FIG. 9A graphs the release of entrapped 6-Carboxyfluorescein (CF) from liposomes (90:10 DPPC:MPPC incorporated with 5 mol % of DSPE-PEG2000) in the presence of PBS and as a function of temperature (37° C.—open circle; 38° C.—closed square; 39° C.—closed triangle; 39.5° C.—open triangle; and 40° C.—closed circle).
Figure 9B:
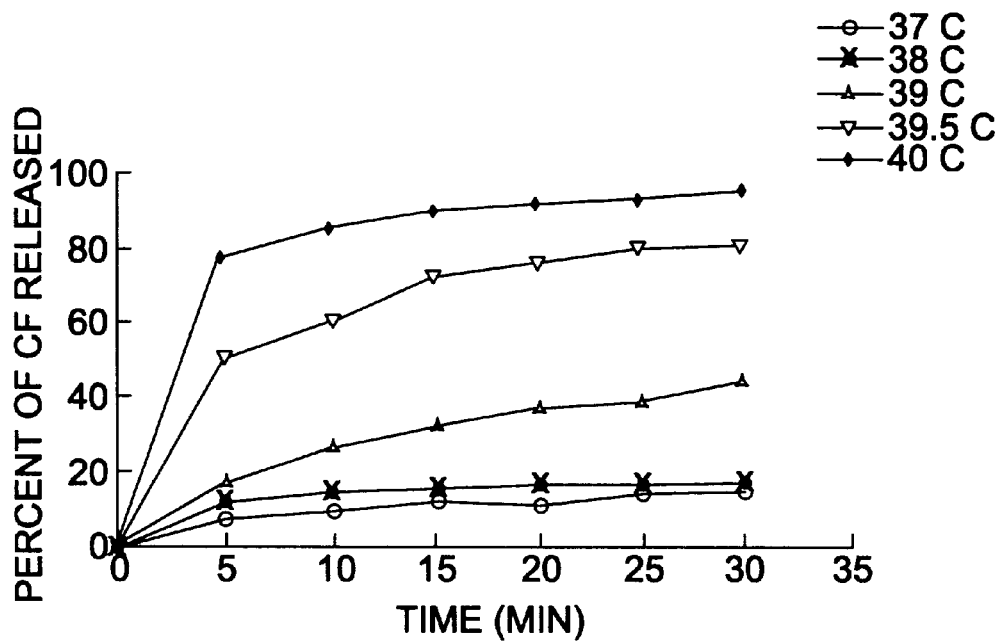
FIG. 9B graphs the release of entrapped 6-Carboxyfluorescein (CF) from liposomes (composed of 90:10 DPPC:MPPC and incorporated with 5 mol % of DSPE-PEG2000) in the presence of 50% bovine serum and as a function of temperature (37° C.—open circle; 38° C.—closed square; 39° C.—closed triangle; 39.5° C.—open triangle; and 40° C.—closed circle).
Figure 10:
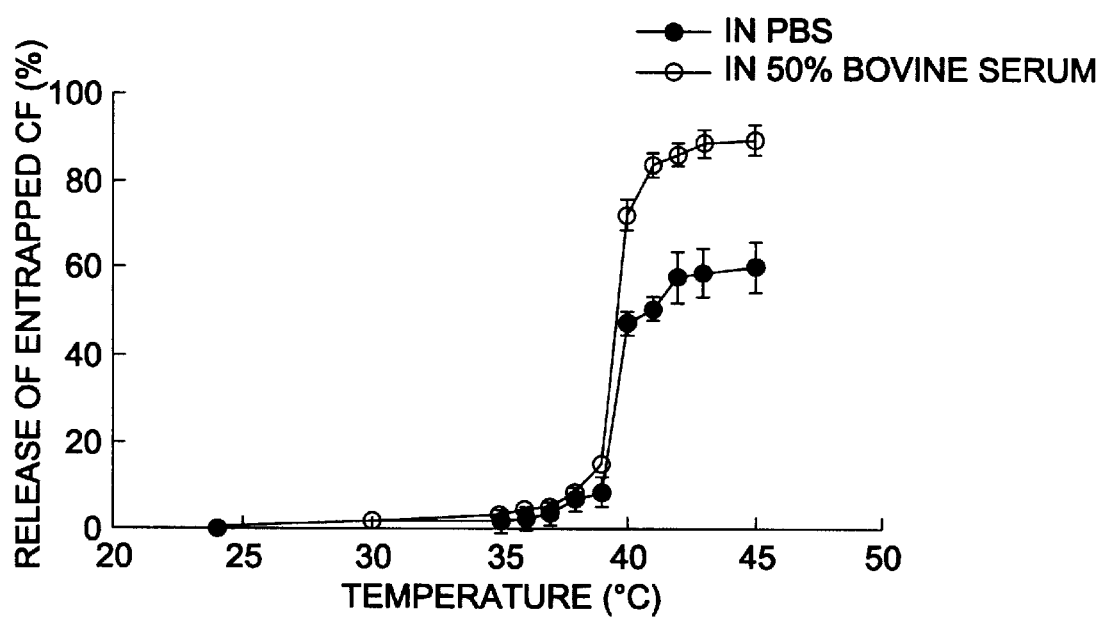
FIG. 10 graphs the cumulative release of entrapped 6-Carboxyfluorescein (CF) from liposomes composed of 90:10 DPPC:MPPC, at various temperatures from 25° to 45° C. in the presence of PBS (closed circles) or 50% bovine serum (open circles).

FIG. 9A shows the release of entrapped CF at 37° to 40° C. as a function of time, in the presence of PBS. FIG. 9B shows the release of entrapped CF at 37° to 40° C. as a function of time, in the presence of 50% bovine serum. The surface modified liposome formulation of the present invention was stable at physiological temperature (37° C.) in the presence of PBS and serum, showing 1% and 7% of CF release, respectively. However, incubation of these liposomes at 40° C. showed 64% (in PBS) and 76% (in serum) release of entrapped CF after five minutes of incubation, and reached 77% (in PBS) and 92% (in serum) after 30 minutes' incubation. Cumulative release profiles of entrapped CF from liposomes in the presence of PBS and 50% bovine serum showed 58% and 73% release, respectively (FIG. 10). While not wishing to be held to a single theory, the enhanced release of CF in the presence of serum could be attributable to the interaction of certain small molecule blood components in the serum with the liposome surface.

The foregoing examples are illustrative of the present invention, and are not to be construed as limiting thereof. The invention is described by the following claims, with equivalents of the claims to be included therein.

That which is claimed is:

1. A liposome containing an active agent entrapped within the liposome interior space, said liposome having a gel-phase lipid bilayer membrane comprising phospholipid which is dipalmitoylphosphatidylcholine (DPPC) and lysolipid which is monopalmitoylphosphatidylcholine (MPPC), wherein phospholipid and lysolipid are contained in the bilayer membrane in a ratio of from 99:10 to 80:20 by molar weight and wherein phospholipids are the primary lipid source for the lipid bilayer membrane and wherein lysolipid is contained in the bilayer membrane in an amount sufficient to increase the percentage of active agent released at the phase transition temperature compared to that which would occur in the absence of said lysolipid.

2. A liposome according to claim 1 having a diameter of from about 50 nanometers to about 400 nanometers.

3. A liposome according to claim 1, wherein the liposome bilayer further comprises phospholipid derivatized with a hydrophilic polymer.

4. A liposome according to claim 3, wherein said hydrophilic polymer is selected from the group consisting of polyethylene glycol, polylactic acid, polyglycolic acid, copolymers of polylactic acid and polyglycolic acid, and polyvinyl alcohol.

5. A liposome according to claim 1, wherein said active agent is a pharmacologically active agent, a flavor agent, a diagnostic agent, or a nutritional agent.

6. A liposome according to claim 1, wherein said active agent is a pharmacologically active agent selected from the group consisting of antineoplastic agents, anti-inflammatory agents, immunosuppressive agents, antibiotic agents and anti-infective agents.

7. A liposome according to claim 1, wherein said active agent is selected from the group consisting of methotrexate, doxorubicin, epirubicin, daunorubicin, vincristine, vinblastine, etoposide, ellipticine, camptothecin, paclitaxel, docetaxol, cisplatin, prednisone, methyl-prednisone, and ibuprofen.

8. A liposome according to claim 1, wherein said active agent is paclitaxel.

9. A liposome according to claim 1, wherein said active agent is camptothecin.

10. A liposome containing an active agent entrapped within the liposome interior space and having a gel-phase lipid bilayer membrane comprising a phospholipid which is dipalmitoylphosphatidylcholine (DPPC) and lysolipid which is monopalmitoylphosphatidylcholine (MPPC), wherein phospholipids are the primary lipid source for the lipid bilayer membrane, and wherein phospholipid and lysolipid are contained in the bilayer membrane in a ratio of from 90:10 to 80:20 by molar weight.

11. A liposome according to claim 10, wherein said active agent is a pharmacologically active agent, a flavor agent, a diagnostic agent, or a nutritional agent.

12. A liposome according to claim 10, wherein said active agent is a pharmacologically active agent selected from the group consisting of antineoplastic agents, anti-inflammatory agents, immunosuppressive agents, antibiotic agents and anti-infective agents.

13. A liposome according to claim 10, wherein said active agent is selected from the group consisting of methotrexate, doxorubicin, epirubicin, daunorubicin, vincristine, vinblastine, etoposide, ellipticine, camptothecin, paclitaxel, docetaxol, cisplatin, prednisone, methyl-prednisone, and ibuprofen.

14. A liposome according to claim 10, wherein said active agent is paclitaxel.

15. A liposome according to claim 10, wherein said active agent is camptothecin.

16. A method of administering an active agent to a preselected hyperthermic target site in a subject, the improvement comprising:
    entrapping said active agent in the aqueous interior of a liposome, said liposome having a gel-phase lipid bilayer membrane comprising phospholipid which is dipalmitoylphosphatidylcholine (DPPC) and lysolipid which is monopalmitoylphosphatidylcholine (MPPC), wherein phospholipids are the primary lipid source for the lipid bilayer membrane, and wherein the aqueous interior of the liposome further comprises lysolipid in an equilibrating amount to the lysolipid contained in the lipid bilayer, and wherein phospholipid and lysolipid are contained in the bilayer membrane in a ratio of from 90:10 to 80:20 by molar weight.

17. A method according to claim 16, wherein said active agent is also entrapped within the lipid bilayer membrane.

18. A method according to claim 16, wherein said liposome bilayer further comprises phospholipid derivatized with a hydrophilic polymer.

19. A method according to claim 18, wherein said hydrophilic polymer is selected from the group consisting of polyethylene glycol, polylactic acid, polyglycolic acid, copolymers of polylactic acid and polyglycolic acid, and polyvinyl alcohol.

20. A method according to claim 16, wherein said active agent is a pharmacologically active agent, a diagnostic agent, or a nutritional agent.

21. A method according to claim 16, wherein said active agent is a pharmacologically active agent selected from the group consisting of antineoplastic agents, anti-inflammatory agents, immunosuppressive agents, antibiotic agents and anti-infective agents.

22. A method according to claim 16, wherein said active agent is selected from the group consisting of methotrexate, doxorubicin, epirubicin, daunorubicin, vincristine, vinblastine, etoposide, ellipticine, camptothecin, paclitaxel, docetaxol, cisplatin, prednisone, methyl-prednisone, and ibuprofen.

23. A method according to claim 16, wherein said active agent is paclitaxel.

24. A liposome according to claim 16, wherein said active agent is camptothecin.

* * * * *

UNITED STATES PATENT AND TRADEMARK OFFICE
CERTIFICATE OF CORRECTION

PATENT NO. : 6,200,598 B1
DATED : March 13, 2001
INVENTOR(S) : David Needham

It is certified that error appears in the above-identified patent and that said Letters Patent is hereby corrected as shown below:

<u>Column 1,</u>
Add the following to the first paragraph:
-- This invention was made with Government support under National Cancer Institute SPORE Grant No. CA42745.

Signed and Sealed this

Sixth Day of November, 2001

Attest:

NICHOLAS P. GODICI
Attesting Officer
Acting Director of the United States Patent and Trademark Office